(12) United States Patent
Gnos et al.

(10) Patent No.: US 6,629,976 B1
(45) Date of Patent: Oct. 7, 2003

(54) RADIUS MARROW NAIL

(75) Inventors: Robert Gnos, Laupen (CH); Kamel Guelmi, Paris Cedex (FR)

(73) Assignee: Sulzer Orthopedics, Ltd., Baar (CH)

( * ) Notice: Subject to any disclaimer, the term of this patent is extended or adjusted under 35 U.S.C. 154(b) by 113 days.

(21) Appl. No.: 09/656,600

(22) Filed: Sep. 7, 2000

(30) Foreign Application Priority Data

Nov. 1, 1999 (EP) ............................................. 99810989

(51) Int. Cl.$^7$ ................................................ A61B 17/58
(52) U.S. Cl. ...................................................... 606/62
(58) Field of Search .............................. 606/62, 64, 67

(56) References Cited

U.S. PATENT DOCUMENTS

| | | | | |
|---|---|---|---|---|
| 4,475,545 A | * | 10/1984 | Ender ........................... | 606/64 |
| 4,827,917 A | * | 5/1989 | Brumfield ..................... | 606/64 |
| 4,913,137 A | * | 4/1990 | Azer et al. .................... | 606/64 |
| 5,176,681 A | * | 1/1993 | Lawes et al. .................. | 606/64 |
| 5,531,748 A | * | 7/1996 | de la Caffiniere ............. | 606/62 |
| 5,658,287 A | * | 8/1997 | Hofmann et al. ............. | 606/63 |
| 5,658,288 A | * | 8/1997 | Kim .............................. | 606/64 |
| 5,935,127 A | * | 8/1999 | Border ......................... | 606/62 |

FOREIGN PATENT DOCUMENTS

| | | |
|---|---|---|
| DE | 9115201.1 | 3/1992 |
| EP | 0202141 A2 | 11/1986 |
| WO | WO 99/35989 | 7/1999 |

* cited by examiner

*Primary Examiner*—Eduardo C. Robert
*Assistant Examiner*—David Comstock
(74) *Attorney, Agent, or Firm*—Townsend and Townsend and Crew, LLP

(57) ABSTRACT

A marrow nail for the distal region of a radius bone. The marrow nail has a radius of curvature R between 100 and 1000 mm in order that it can be introduced adjacently to the distal articular surfaces of the radius bone, and an inclined transverse bore which crosses the marrow nail at a distance of less than 30 mm ahead of its end in order also to grasp bone fragments of fractures which extend transversely through the distal bearing surface. The end of the marrow nail is formed as a securing head for an aiming device for transverse bores.

7 Claims, 2 Drawing Sheets

RADIUS MARROW NAIL

BACKGROUND OF THE INVENTION

The invention relates to a radius marrow nail which did not previously exist in the form proposed.

Bone fractures in the vicinity of the wrist joint occur relatively frequently. Especially in older persons the feeling for one's equilibrium becomes poorer, the hands are used more for support and at the same time a weakening of the bones takes place. The result is fractures of the radius bone in the vicinity of the articular surfaces to the wrist joint, i.e. to the scaphoid and to the lunate bone. These fractures arise as shearing beneath the articular surfaces or pass transversely through the articular surfaces. The previous treatment methods consisted in the application of bone plates and/or bone screws or in the application of a plaster cast with the risk that the bone fragments do not exactly grow together in an ideal position.

SUMMARY OF THE INVENTION

It is an object of the invention to create a reliable splinting for fractures of the radius bone in the vicinity of the wrist joint. This object is satisfied by a radius marrow nail having a curvature of its longitudinal axis corresponding to an average radius of curvature 100<R<1000 mm, having a securing head for an aiming device and having an inclined transverse bore which crosses the longitudinal axis at a distance of less than 30 mm from the end of the securing head.

The advantage of this marrow nail lies in that it can be introduced outside the articular surface for the scaphoid at the styloid process and permits the introduction of a bone screw for fixing and securing directly beneath the articular surfaces in the region of the greatest transverse extent. In this the marrow nail which is anchored in the radius bone serves as a reference for the bone fragments to be secured. A further advantage lies in that through the splinting from within only minor external lesions need be made for the entry of marrow nails and for securing screws.

In accordance with aspects of the present invention, it is advantageous to provide radius marrow nails of different lengths with lengths of from 50 to 200 mm and with different diameters of from 3 to 10 mm in order to cover the spectrum of different patients. In order not to unnecessarily weaken the securing head for the securing of a hammering-in and aiming apparatus and for the provision of the inclined transverse bore, it is provided with a larger outer diameter than the rest of the radius marrow nail. The transverse bore can form an angle a between 40° and 70° with the shaft axis of the securing head in order to cross a region close beneath the joint sockets in the distal region of the radius bone with the transverse bore and in order also to grip bone fragments of fractures through the joint sockets. With an angle a between 55° and 65° the transverse bore can be displaced distally to such an extent that its longitudinal axis crosses the securing head at a distance of less than 15 mm ahead of its end. A further transverse bore for anchoring the radius marrow nail is provided in its tip. Body-compatible metals, for example chromium-cobalt-nickel alloys in accordance with ISO 5832-1, or titanium alloys, are suitable as material for the radius marrow nail. For introducing the marrow nail an awl, of which the frontal region corresponds to the radius marrow nail with respect to its outer diameter and the curvature of its longitudinal axis, is first applied in the vicinity of the styloid process in order to open the marrow nail in the form of a long extended curvature. This has the advantage that the actual articular surfaces to the scaphoid and to the lunatum remain untouched. Then the radius marrow nail can be driven in at its securing head into the radius bone with a sliding hammer. For the securing of the sliding hammer the same thread in the securing head can be used as for an aiming bow which is placed on afterwards. Between the aiming bow and the securing head there is additionally a form-fitted coupling which ensures that transverse bores of the radius marrow nail and associated aiming bores in the aiming bow are aligned with one another. The aiming device and the sliding hammer can also be combined with one another.

Since the transverse bores in the radius marrow nail can have a diameter of only a few millimeters, it is advantageous to bridge over the distance between the aiming bow and the transverse bore with a bore sleeve which is resistant to bending. At the same time a borer receives in this way a substantially longer and more precise guiding, which can amount to more than eight times the diameter of the borer. The bore sleeves are removable in order that they do not hinder the securing of the aiming bow and can be driven forwards after its securing to such an extent that they receive a support in the radius bone with their sharpened front edge.

The invention will be described in the following with reference to exemplary embodiment.

DETAILED DESCRIPTION OF SPECIFIC EXEMPLARY EMBODIMENTS

In the figures a marrow nail for the distal region of a radius bone is shown. The marrow nail has a radius of curvature R between 100 and 1000 mm in order that it can be inserted next to the distal articular surfaces of the radius bone, and an inclined transverse bore which crosses the marrow nail at a distance of less than 30 mm ahead of its end in order also to grip bone fragments of fractures which extend transversely through the distal bearing surfaces. The end of the marrow nail is formed as a securing head for an aiming device for transverse bores.

Figure 1:
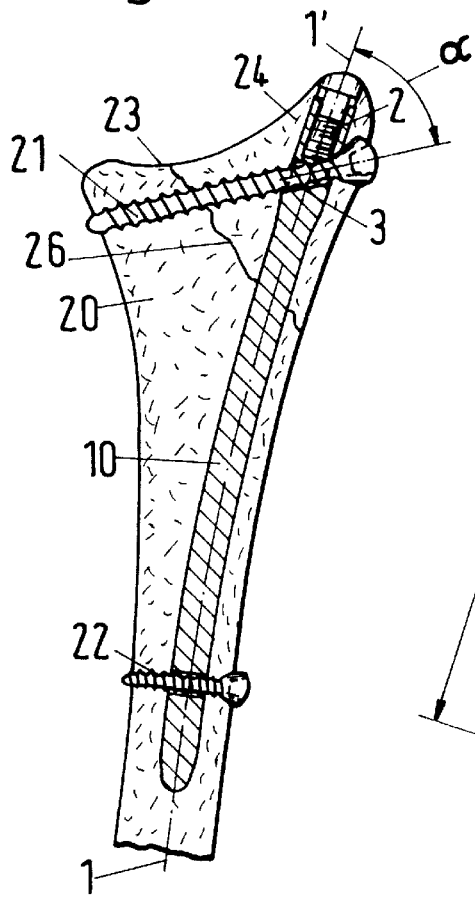
FIG. 1 illustrates, schematically, a longitudinal section through a marrow nail which is inserted in a radius bone.

The reference symbols are used identically in the figures. In FIG. 1a marrow nail 10 extends in a radius bone 20 from its distal end and bridges over a point 26 of fracture. The entry opening for the marrow nail 20 is chosen outside the joint sockets 23, 24 for adjoining wrist joint lunate bones and scaphoid at the styloid process. A bone screw 22 is transversely introduced at the tip of the marrow nail 10 in order to secure the tip in the radius bone 20. The marrow nail 20 itself is curved in the plane of the drawing and is provided at its end which is directed outwardly with a securing head 2 having a straight longitudinal axis 1' as a continuation of the longitudinal axis 1 of the curved region. A second transverse bore 3, which crosses the longitudinal axis 1' of the securing head 2 at an acute angler α, enables the marrow nail to be anchored at the entry side with a further bone screw 21, and in fractures which pass through the bearing shells 23, 24 to additionally fix the fragments to one another.

Figure 2:
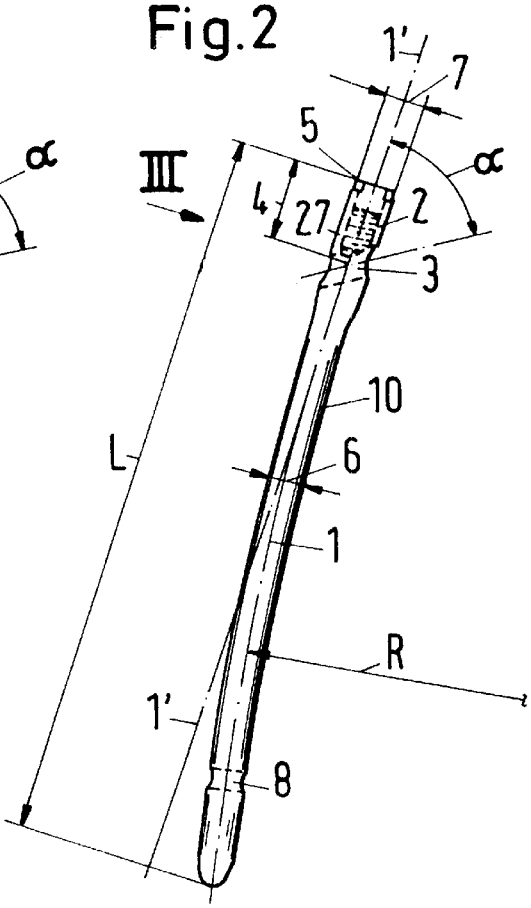
FIG. 2 illustrates, schematically, the radius marrow nail of FIG. 1 in a side view onto the plane in which the curvature of its longitudinal axis lies.
Figure 3:
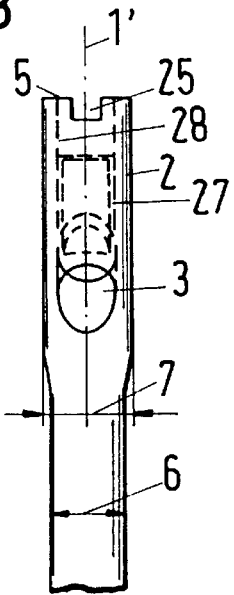
FIG. 3 illustrates, schematically, an enlarged side view of the securing head of FIG. 2 which is rotated by 90°.

The marrow nail 10, as it is illustrated in FIGS. 2 and 3, has an unstretched length L of 100 mm and a radius of curvature R of 350 mm. The diameter 6 of the curved region amounts to 5 mm and the diameter of the securing head 7 amounts to 6 mm. The inclined transverse bore 3 crosses the securing head 2 at a distance 4 of 12 mm from its outer end 5 at an acute angler α of 59°. The transverse bore 3 itself has a diameter of 4 mm, whereas the transverse bore 8 at the tip of the marrow nail 10 has a diameter of 2.7 mm. The outer end 5 is designed as a support surface which is interrupted by a groove 25 in order to be able to align an aiming device 9 with respect to rotation about the longitudinal axis 1'. On the inner side a cylindrical bore 28 is provided in the longitudinal direction with a thread 27 in order to anchor the aiming device 9 or a sliding hammer. In the present example a sliding hammer having a projecting threaded pin is screwed on at the thread 27 of the securing head and the marrow nail is cautiously hammered in.

Figure 4:
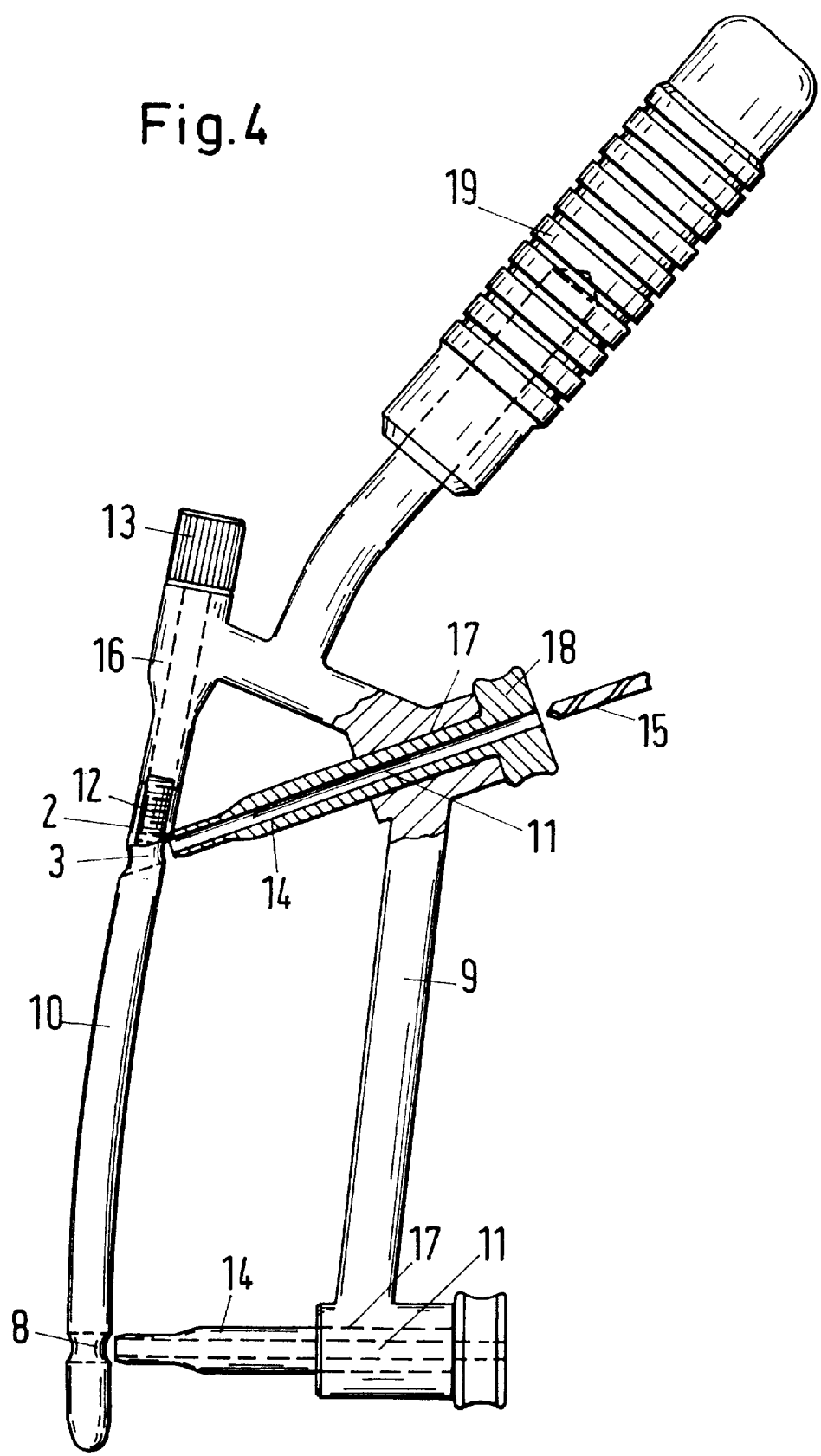
FIG. 4 illustrates, schematically, a side view of a radius marrow nail analogous to FIG. 2 with an aiming device which is secured at the radius marrow nail.

In FIG. 4 a radius marrow nail 10 is coupled to its aiming device 9. The securing is effected at an application piece 16 by means of a securing screw 12 which holds the aiming device 9 with its head 13 and rigidly couples the aiming device to the marrow nail in a predetermined position. The actual aiming device forms a U-shaped bow 9 with laterally projecting grip 19. In alignment with the transverse bores 3, 8 of the marrow nail relatively larger guiding bores 17 are provided in the aiming bow 9, into which longitudinally displaceable bore sleeves 14 can be inserted. The bore sleeves 14 taper at their tip to a thin, beveled bush, which reaches directly up to the marrow nail 10 and which can be supported with its ring-shaped cutting edge at the radius bone. The relatively thin borers 15 which pre-bore the cortical bone in alignment with the transverse bores 3, 8 up to a diameter of aiming bores 11 are guided directly up to the bone and can not depart from the predetermined direction. A guiding of this kind is particularly important in a bore 3 which is inclined to the bone wall. After the pre-boring, the bore sleeves 14 can in each case be drawn out and the suitable bone screws 22, 21 can in each case be applied through the larger guiding bores 17 and turned in. The bore sleeves 14 have in each case a retainer head 18 which limits the tightening in the longitudinal direction and enables its drawing out.

In principle it is also possible to combine the aiming device with a sliding hammer in that for example the head 13 of the securing screw 12 is extended upwardly to such an extent that an inner thread for the threaded pin of a sliding hammer has room. Due to the relatively small dimensions of the marrow nail it must then be observed that the centering surfaces between the application piece 16 and the securing head 2 are not damaged by the hammering in.

What is claimed is:

1. A radius marrow nail adapted to be inserted at the styloid process, the nail comprising a main portion defined by a longitudinal axis, the main portion including a curved region along the longitudinal axis having an average radius of curvature of 350 mm;

a securing head for an aiming device, the securing head having a diameter of 6 mm; and an inclined transverse bore that crosses the longitudinal axis at a distance of approximately 12 mm from its outer end;

wherein the nail has an unstreched length of approximately 100 mm and the curved region has a diameter of approximately 5 mm.

2. A radius marrow nail in accordance with claim 1 wherein the securing head has a diameter that is greater than that of the main portion.

3. A radius marrow nail in accordance with claim 1 wherein the inclined transverse bore forms an angle in a range between 40° and 70° relative to an axis defined by the securing head.

4. A radius marrow nail in accordance with claim 3 wherein the angle lies between 55 and 65 degrees, and wherein the inclined transverse bore crosses the longitudinal axis a distance less than 15 mm from an end portion of the securing head.

5. A radius marrow nail in accordance with claim 1 wherein the radius marrow nail further comprises a second transverse bore located adjacent a tip portion.

6. A radius marrow nail in accordance with claim 1 wherein the radius marrow nail consists of one of a chromium-cobalt-nickel alloy or a titanium alloy.

7. A radius marrow nail in accordance with claim 6 wherein the radius marrow nail consists of a chromium-cobalt-nickel alloy in accordance with ISO 5832-1.

* * * * *